(12) United States Patent
Vogler

(10) Patent No.: US 7,751,452 B2
(45) Date of Patent: Jul. 6, 2010

(54) FIBER LASER ARRANGEMENT

(75) Inventor: Klaus Vogler, Eckental (DE)

(73) Assignee: Quantel Derma GmbH, Erlangen (DE)

( * ) Notice: Subject to any disclaimer, the term of this patent is extended or adjusted under 35 U.S.C. 154(b) by 90 days.

(21) Appl. No.: 11/577,578

(22) PCT Filed: Oct. 12, 2005

(86) PCT No.: PCT/EP2005/010966

§ 371 (c)(1),
(2), (4) Date: Jan. 29, 2008

(87) PCT Pub. No.: WO2006/045437

PCT Pub. Date: May 4, 2006

(65) Prior Publication Data

US 2008/0259970 A1   Oct. 23, 2008

(30) Foreign Application Priority Data

Oct. 20, 2004   (EP) ................... 04024988

(51) Int. Cl.
H01S 3/30  (2006.01)
H01S 3/03  (2006.01)
(52) U.S. Cl. .......................... 372/6; 372/64
(58) Field of Classification Search .......... 372/6
See application file for complete search history.

(56) References Cited

U.S. PATENT DOCUMENTS 5,161,050 A * 11/1992 Grasso et al. .......... 359/341.32
5,207,670 A    5/1993  Sinofsky
6,096,031 A    8/2000  Mitchell et al.
6,110,167 A    8/2000  Cozean et al.
6,350,261 B1   2/2002  Domankevitz et al.
6,620,154 B1   9/2003  Amirkhanian et al.
6,690,685 B1   2/2004  Oliveti et al.
2004/0225283 A1* 11/2004 Nahleili .................. 606/2

FOREIGN PATENT DOCUMENTS

WO   02/091935   11/2002

OTHER PUBLICATIONS

El Sherif, A.F. & King, T.A., "Soft and Hard Tissue Ablation with Short-Pulse High Peak Power and Continuous Thulium-Silica Fibre Lasers," Lasers in Medical Science, Paper No. XP002327261, vol. 18, No. 3 (Sep. 2003).*

Warnaby, C.E., et al., "Photothermal Modeling of Thulium Fibre Laser-Tissue Interactions," Therapeutic Laser Applications and Laser-Tissue Interactions, Munich, Germany (Jun. 2003), Paper No. XP002327262, vol. 5142, No. 1 (Jan. 1998).

(Continued)

*Primary Examiner*—Armando Rodriguez
(74) *Attorney, Agent, or Firm*—Haynes and Boone LLP

(57) ABSTRACT

The present invention provides a system, which comprises a fiber laser (1) for generation of laser radiation, and an applicator (8) coupled with the fiber laser (1), the applicator (8) being adapted for delivery of laser radiation from the fiber laser (1) to an area of interest (22) and comprising an endoscopic fiber (7) or bare fiber (7).

28 Claims, 4 Drawing Sheets

OTHER PUBLICATIONS

Figure 1:
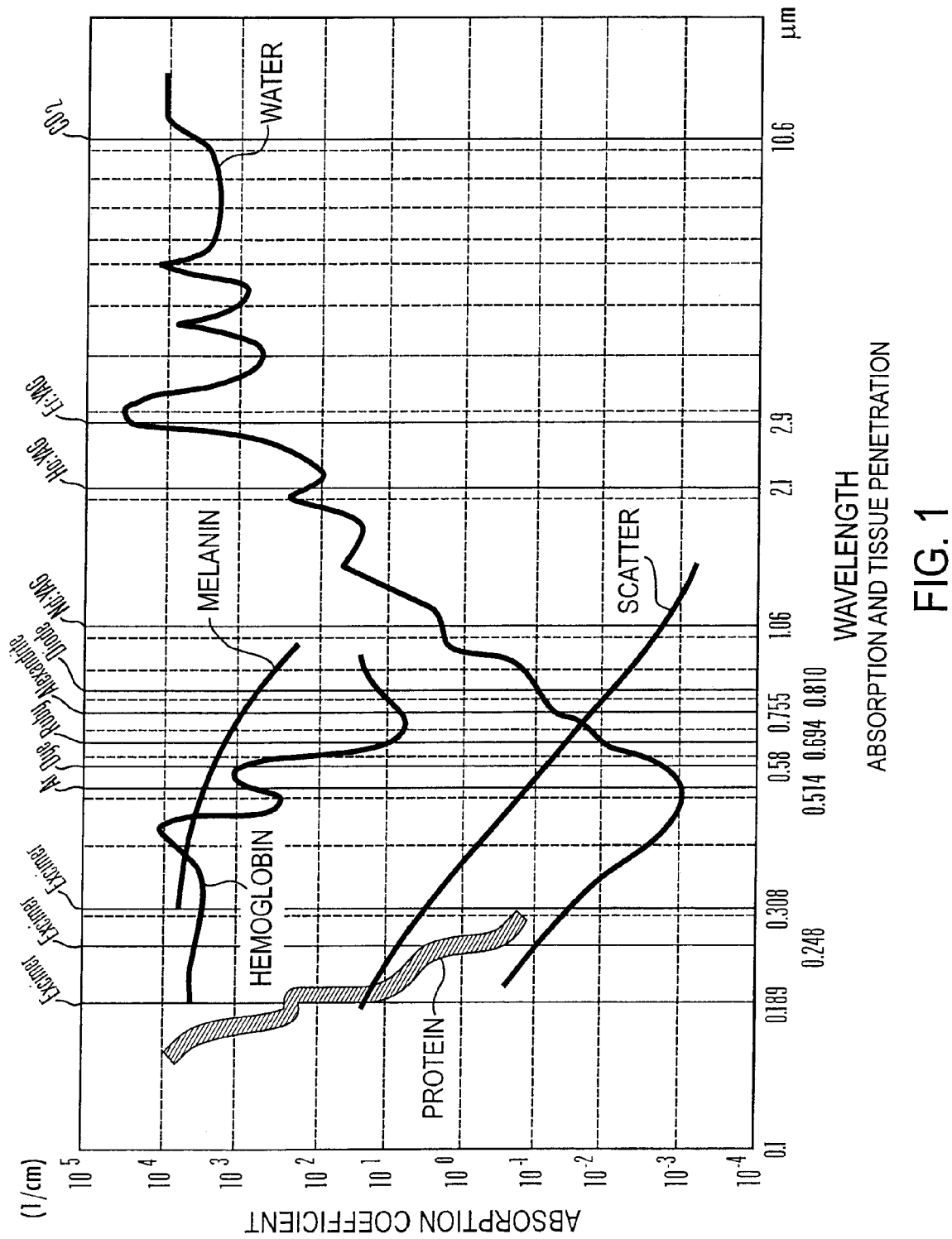

Ghisler, et al., "Tuning of a TM3+HO3+Silica Fiber Laser at 2 um," IEEE Journal of Quantum Electronics, IEEE Inc, New York, Paper No. XP000541532, vol. 31, No. 11 (Nov. 1995).

Naruse, K., et al. "Development for Medical Surgical System with Function Variability and Flexible Delivery Using Dual-Wavelength Infrared Fiber Laser," Laser Tissue Interaction XIII: Photochemical, Photothermal, and Photomechanical (Jan. 20-23, 2002), San Jose, California, Paper No. XP002327263, vol. 4617 (Jan. 2002).

Ghisler, C.H., et al., "Cladding-Pumping of a Tm<3+>:Ho<3+> Silica Fibre Laser," Optics Communications, North-Holland Publishing Co., Amsterdam, Illinois, Paper No. XP004013984, vol. 132, No. 5 (Dec. 1996).

Weber, H.P., et al., "Fibre Lasers for Surgery," Conf Lasers Electro Opt Eur Tech Dig; Conference on Lasers and Electro-Optics Europe-Technical Digest 1996, p. 300, Paper No. XP002327264 (1996).

Myslinski, P., et al., "Q-Switched Thulium-Doped Fiber Laser," Optical Engineering, Soc. of Photo-Optical Instrumentation Engineers, Bellingham, US, Paper No. XP000396818, vol. 32, No. 9, pp. 2025-2029 (Sep. 1993).

Myslinski, P, et al., "Applications of Rare-Earth-Doped Fibres," Proceedings of the Instrumentation and Measurement Technology Conference, Orvine, CA, May 18-20, 1993, pp. 290-294, Paper No. XP010131500 (May 1993).

Sahu, J.K., et al., "Tunable Tm-Doped Silica Fibre Laser," Lasers and Electro-Optics Europe, 2003. Cleo/Europe. 2003 Conference on Munich, Germany Jun. 22-27, 2003, Piscataway, NJ, pp. 621-622, Paper No. XP010711869 (Jun. 22, 2003).

Hayward, R.A., et al., "Efficient Cladding-Pumped Tm-Doped Silica Fibre Laser with High Power Singlemode Output at 2 µm" Electronics Letters, IEE Stevenage, GB,vol. 36, No. 8, pp. 711-712, Paper No. XP006015130 (Apr. 13, 2000).

Katzir, A., Ed., Thompson, B.J., "Optical Fiber Techniques (Medicine)" Selected Papers on Optical Fibers in Medicine, SPIE Milestone Series, Bellingham, SPIE, US, vol. MS 11, pp. 3-19, Paper No. XP000467426 (1990).

Beaghler, Marc, A., et al., "Urological Applications of the Holmium Laser," Proc SPIE Int Soc Opt Eng; Proceedings of Spie—The International Society for Optical Engineering, vol. 3245, pp. 117-119, Paper No. XP002327265 (1997).

* cited by examiner

FIBER LASER ARRANGEMENT

This application is a 371 of PCT/EP2005/010966 filed on 12 Oct. 2005, which claims priority from European Patent Application No. 04024988.0 filed 20 Oct. 2004, the entireties of which are incorporated by reference herein.

FIELD OF THE INVENTION

The present invention generally relates to laser systems, and, particularly, to systems comprising fiber lasers.

BACKGROUND OF THE INVENTION

Holmium-lasers (Ho-lasers) emitting laser beams having a wavelength of 2.1 µm are suitable for various medical applications, especially in minimal-invasive or endoscopic surgery. A wavelength of 2.1 µm and the pulsed emission characteristics of Ho-lasers (e.g. a Holmium-Yttrium-Aluminium-Garnet-laser, Ho:YAG-laser) are suitable for precisely localized tissue ablation without conflicting thermal side effects in surrounding volume.

The capacity of precisely localized treatments and the confinement of radiation energy within an area of interest is determined by two facts:

Water has a strong absorption coefficient at a wavelength of 2.1 µm wherein the water absorption coefficient characterizes tissue ablation characteristics because human tissue contains about 80% water (see FIG. 1).

High transmission rate of a laser beam having a wavelength of 2.1 µm through silica fibers having a low or no water content up to a treatment region.

Known Ho-laser systems for minimal-invasive surgery comprise a Ho-laser, a transmission fiber for transmission of the laser beam from the Ho-laser, a coupling unit coupling the Ho-laser and the transmission fiber and an end piece connected to the transmission fiber for delivering the laser beam to a treatment region.

Known Ho-laser systems for minimal-invasive applications provide laser beams having a power of 20 W and more. A typical transmission fiber has a diameter of 400 µm and more for use, e.g., in the treatment of Benign Prostate Hyperopia (BPH) and lithotripsy.

Known systems however exhibit several problems. Coupling of pulsed high-energy laser radiation having a wavelength of 2.1 µm into a transmission fiber having a small diameter is critical and troublesome and results in maintenance problems and degradation of involved components. Ho-laser systems require extensive cooling and space for system accommodation. Further, pulsed laser radiation provided by Ho-laser systems is not suitable for several minimal-invasive applications due to shock waves produced by pulsed laser radiation.

OBJECT OF THE INVENTION

The object of the present invention is to overcome the above drawbacks of known systems and to provide an improved laser-based arrangement for minimal-invasive procedures.

SUMMARY OF THE INVENTION

To solve the above object, the present invention provides a system, which comprises a fiber laser for generation of laser radiation, and an applicator coupled with the fiber laser, the applicator being adapted for delivery of laser radiation from the fiber laser to an area of interest and comprising an endoscopic fiber or bare fiber.

Further, the present invention provides an apparatus which comprises an endoscopic fiber or bare fiber a an applicator and a fiber laser for generation of laser radiation, the applicator for delivering laser radiation from the fiber laser to an area of interest.

Further embodiments of the present invention are defined in the dependent claims.

SHORT DESCRIPTION OF THE DRAWINGS

Figure 2:
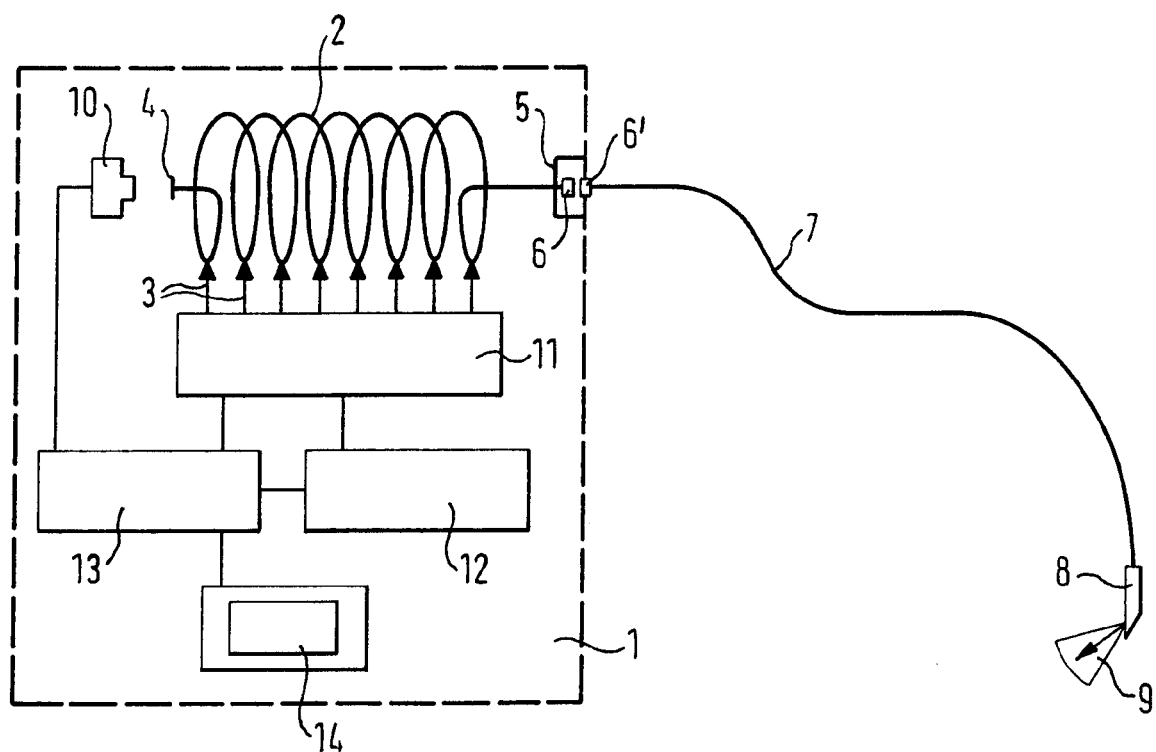
Figure 3:
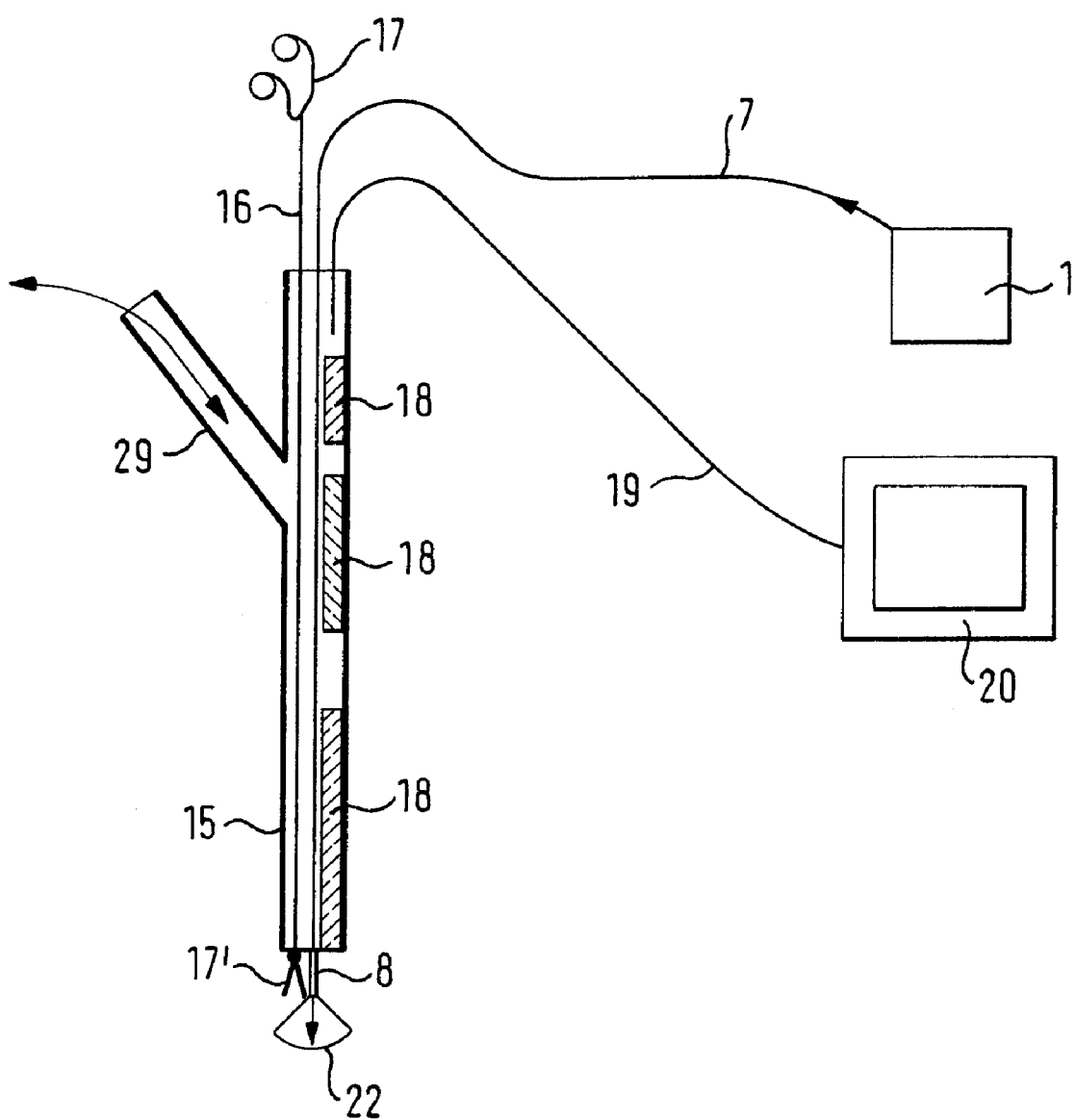

The above set forth and other features and aspects of the present invention are more apparent from the detailed description of the present invention read in conjunction of the attached drawings, wherein:

FIG. 1 is a draft showing absorption coefficients of different substances and fluids versus laser radiation wavelengths, FIG. 2 schematically illustrates an embodiment of the present invention and FIG. 3 schematically illustrates a further embodiment of the present invention.

Figure 4:
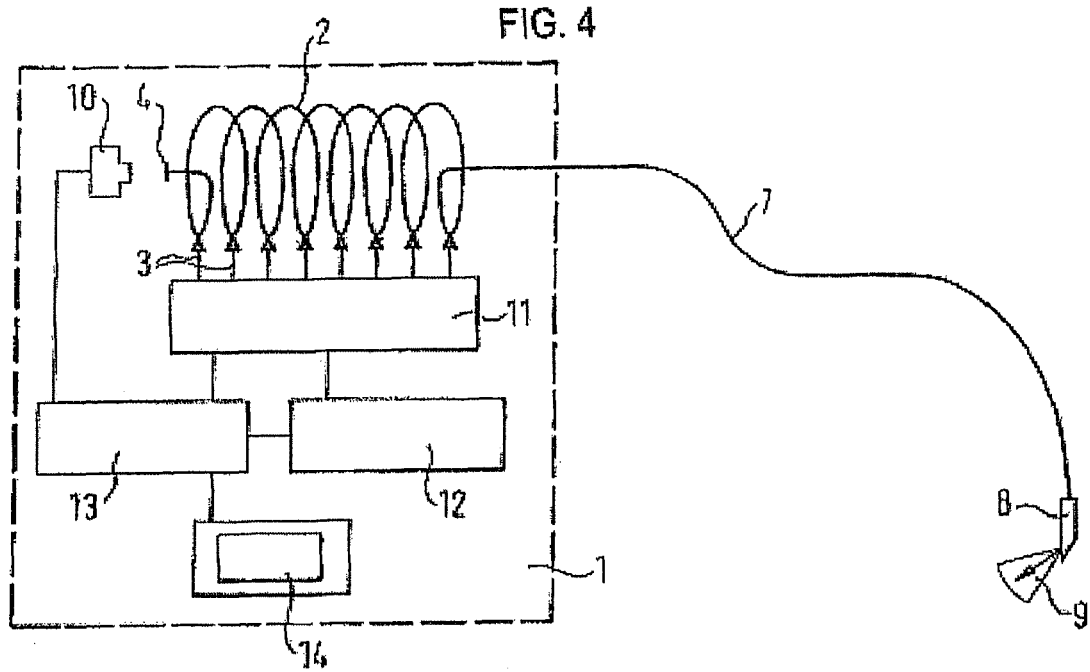

FIG. 4 schematically illustrates a further embodiment of the present invention.

DETAILED DESCRIPTION OF THE INVENTION

As illustrated in FIG. 2, an embodiment comprises a fiber laser 1. The fiber laser 1 comprises, as active or lasing medium, a doped active fiber 2.

Examples for doped active fiber 2 include Thallium doped fibers (Tm-doped fibers) and fibers having different dopings enabling generation of laser radiation having a wavelength in a range around 2.0µm (or 1.5 µm to 3.0 µm. The wavelength can be, e.g., in the range of 1.92 µm to 1.96 µm, such as 1.94 µm.

As can be derived from FIG. 1, such a radiation wavelength improves precisely localized treatments and the confinement of radiation energy within an area of interest because the water absorption coefficient at a wavelength of 2.0 µm is even higher than the water absorption coefficient effective in prior approaches.

For pumping active fiber 2, laser diodes 3 are provided. Although several laser diodes 3 are shown in FIG. 2, a single laser diode 3 can be sufficient. One aspect determining the number of laser diodes 3 is a laser power and its scaling, respectively, to be generated by fiber laser 1. Laser diodes 3 pump active fiber 2 by emitting respective pump radiation, suitable for corresponding absorption bands of fiber dopants.

On an end face 4, active fiber 2 is polished and coated such end face 4 provides the function of a mirror, e.g. a high reflectivity mirror serving as rear mirror of fiber laser 1. Opposite end face 4, an energy monitor 10 is arranged by means of which laser energy generated in active fiber 2 can be monitored.

Information provided by energy monitor 10 can be used by controller 13 to operate fiber laser 1 such that desired/required laser radiation is generated. Controller 13 further controls a power supply 11, which supplies power for laser diodes 3. Power supply 11 can be, for example, a low voltage power supply such as a 24V power supply.

A central power supply 12 supplies power to all components of fiber laser 1 requiring power supply. Although FIG. 2 merely illustrates connections between central power supply 12, on the one hand, and power supply 11 and controller 13, on the other hand, central power supply 12 can be also connected to energy monitor 10 and/or a display 14. Further, central power supply 12 and power supply 11 can be replaced by a single power supply providing power to each component of fiber laser 1 requiring power supply.

Display 14, which can include a touch screen for operating fiber laser 1, provides operational information of fiber laser 1 to an operator. Although not shown, fiber laser 1 can comprise an input interface (i.e. keyboard, buttons, sliders, etc.) for controlling fiber laser 1. Such an input interface can be used in addition or as alternative to a touch screen provided by display 14.

The system illustrated in FIG. 2 comprises a transmission fiber 7 for transmission of laser radiation generated by fiber laser 1 to an applicator 8. The length of transmission fiber 7 depends upon the application to be carried out and can range, for example, form a few centimeters to several meters. In FIG. 2, transmission fiber 7 is illustrated as being flexible over its entire length. However, transmission fiber 7 can include rigid portions. For example, transmission fiber's 7 end portion coupled with applicator 8 can be rigid in order to support insertion into a channel of an endoscope and/or handling of applicator 8. The end portion of transmission fiber 7, which receives laser radiation from the fiber laser device 1, can be formed from a rigid material.

Applicator 8 receives a laser radiation generated by fiber laser 1 via transmission fiber 7 and emits laser radiation into an area of interest 9.

Coupling of transmission fiber 7 and fiber laser 1 can be accomplished in different ways. As illustrated in FIG. 2, this coupling can include a coupling portion 5 arranged in a housing of fiber laser 1. Coupling portion 5 serves to accommodate the end of fiber 2 opposite its end face 4. The end of active fiber 2 arranged in coupling portion 5 can comprise a connector 6 for connection with transmission fiber 7. Transmission fiber 7 can comprise a connector 6' for connection with connector 6. Connectors 6 and 6' can be designed such that the respective end faces of active fiber 2 and transmission fiber 7 can be brought into close contact for transmission of laser radiation from active fiber 2 into transmission fiber 7. Coupling of active fiber 2 and transmission fiber 7 can be also accomplished by splicing at least one of the fibers.

According to an aspect of the present invention, the diameters of active fiber 2 and transmission fiber 7 are of comparable size, e.g. equal size. This allows an easy coupling of fibers 2 and 7 by simple contact coupling via the respective fiber front faces or by splicing. Possible diameters for fibers 2 and 7 include diameters in the range of 200 μm to 600 μm and diameters of about 200 μm, about 100 μm, and about 50 μm and smaller. Such fiber diameters are especially suitable for endoscopic applications in the field of neurosurgery.

As shown in FIG. 4, coupling of active fiber 2 and transmission fiber 7 is not required if fibers 2 and 7 are formed as a single fiber. According to this aspect, a portion of such a single fiber serves as active fiber 2, while the remaining fiber portion serves as transmission fiber 7.

However, using separate fibers 2 and 7 being coupled with each other can also yield good results. Compared, for example, with a Ho-laser, fiber laser 1 does not suffer from thermal load and thermal lensing. As a result, the beam parameter product is extremely good enabling an easy coupling of active fiber 2 and transmission fiber 7 even if the fibers' diameters are different. For example, coupling of transmission fiber 7 having a diameter smaller than the diameter of active fiber 2 does not represent a problem as compared with prior approaches. Further, since fiber laser 1 exhibits no thermal lensing and, thus, no pointing stability issues, coupling of laser radiation more than 10 W into transmission fiber is easily possible even if transmission fiber 7 has a diameter of less than 200 μm.

Fiber laser 1 can be operated to generate pulsed laser radiation and/or continuous laser radiation (continues wave emission, cw emission). Pulsed emission of fiber laser 1 can be software controlled to generate, for example, laser pulses having a duration in the range of 0.5 ms to 20 ms, e.g. of about 1 ms. Operating fiber laser 1 in a pulsed mode is suitable for applications such as lithotripsy of kidney stones or stones in the gall bladder, endoscopic microsurgery or treatments concerning BPH.

Operating fiber laser 1 in a continuous wave emission mode can be used, for example, in sensitive microsurgery (e.g. neurosurgery) where acoustic-shock waves usually produced by pulsed laser radiation have to be prevented.

Fiber laser 1 can generate laser radiation energy in the range of 5 W to 50 W, e.g. a 10 W laser radiation energy. Possible duty cycles of fiber laser 1 can be in the range of 10% to 50%.

Another embodiment illustrated in FIG. 3 provides an apparatus comprising fiber laser 1, transmission fiber 7 and applicator 8 described in greater detail with reference to FIG. 2. The apparatus according to FIG. 3 further comprises an endoscope 15 having channels (not referenced) for instrumentation 16, observation optics 17, transmission fiber 7 etc. For example, instrumentation 2 can be an endoscopic scissor having handles 17 on its proximal end and tiny scissors 17' on its distal end.

Observation optics 18 arranged in an channel of endoscope 15 can comprise individual rod lenses for imaging objects at the distal end of endoscope 15. Images provided by observation optics 18 can be displayed via an optical fiber 19 on a monitor 20.

Endoscope 15 can further comprise a channel 29 to remove fluids and cutted tissue using, for example, a fluid pump (not illustrated) being in connection with channel 21.

Through one of the channels of endoscope 15, transmission fiber 7 and applicator 8 can be guided for insertion via endoscope 15 towards an endoscopic area of interest 22.

The invention claimed is:

1. System, comprising:
   a fiber laser for generation of laser radiation, the fiber laser comprising:
      an active fiber coiled within a housing, and
      a plurality of laser diodes positioned within the housing, the plurality of laser diodes in communication with the active fiber in order to pump the active fiber with radiation; and
   an applicator coupled with the fiber laser, the applicator being adapted for delivery of laser radiation from the fiber laser to an area of interest the applicator comprising an endoscopic fiber or bare fiber.

2. System according to claim 1, wherein the endoscopic or bare fiber is coupled with the fiber laser and the applicator for transmission of laser radiation from the fiber laser to the applicator.

3. System according to claim 1, wherein the active fiber comprises a doped fiber as active medium for generation of laser radiation having a wavelength in the range of 1.6 μm to 2.4 μm.

4. System according to claim 3, wherein
   the active fiber is a Thulium doped fiber, and
   the active fiber has a diameter in the range of 5 μm to 600 μm.

5. System according to claim 3 wherein
the active fiber comprises a first connector, and the endoscopic or bare fiber comprises a second connector for coupling with the first connector of the active fiber.

6. System according to claim 3, wherein the endoscopic or bare fiber and the active fiber are formed by a single fiber.

7. System according to claim 1, further comprising at least one of the following:
wherein the fiber laser is adapted for generation of laser radiation having a laser energy in the range of 5 W to 30 W,
wherein the fiber laser is adapted for generation of pulsed laser radiation having a pulse duration in the range of 0.5 ms to 20 ms,
wherein the fiber laser has a duty cycle in the range of 10% to 100%, or
wherein the fiber laser is adapted for generation of continuous laser radiation.

8. Medical treatment apparatus, comprising:
an endoscopic fiber or bare fiber as an applicator, and
a fiber laser having an active fiber for generation of laser radiation,
the applicator for delivery of laser radiation from the fiber laser to an area of interest.

9. Medical treatment apparatus according to claim 8, further comprising an endoscope, the applicator being arranged at a distal end of the endoscope.

10. Medical treatment apparatus according to claim 9, further comprising at least one of the following:
wherein the endoscopic or bare fiber is sized and shaped to be guided through the endoscope,
wherein the endoscope comprises a laser radiation delivery channel, and the endoscopic or bare fiber is arranged in the laser radiation delivery channel,
wherein the endoscope comprises an instrumentation channel for accommodation of at least one endoscopic instrument to be guided through the endoscope,
wherein the endoscope comprises observation optics,
wherein the endoscope comprises a channel for removing at least one of fluid and tissue, or
wherein the endoscope is at least partially flexible.

11. Medical treatment apparatus according to claim 8, wherein the active fiber comprises a doped fiber as active medium for generation of laser radiation having a wavelength in the range of 1.6 µm to 2.4 µm.

12. Medical treatment apparatus according to claim 11, further comprising at least one of the following:
wherein the active fiber is a Thulium doped fiber,
wherein the active fiber has a diameter in the range of 5 µm to 600 µm,
wherein the fiber laser comprises a first connector for coupling with the endoscopic or bare fiber,
wherein the endoscopic or bare fiber comprises a second connector for coupling with a first connector of the fiber laser, or
wherein the endoscopic or bare fiber and the active fiber are coupled by a contact coupling via fiber front faces of the endoscopic or bare fiber and the active fiber or by splicing of at least one of the endoscopic or bare fiber and the active fiber.

13. Medical treatment apparatus according to claim 8, wherein the endoscopic or bare fiber and the active fiber are formed by a single fiber.

14. Medical treatment apparatus according to claim 8, further comprising at least one of the following:
wherein the fiber laser is adapted for generation of laser radiation having a laser energy in the range of 5 W to 50 W,
wherein the fiber laser is adapted for generation of pulsed laser radiation having a pulse duration in the range of 0.5 ms to 20 ms, or
wherein the fiber laser has a duty cycle in the range of 10% to 100%.

15. System according to claim 2, wherein the active fiber comprises a doped fiber as active medium for generation of laser radiation having a wavelength in the range of 1.6 µm to 2.4 µm.

16. System according to claim 3, wherein the laser radiation has a wavelength in the range of 1.92 µm to 1.94 µm.

17. A system comprising:
a fiber laser for generation of laser radiation, and
an applicator coupled with the fiber laser, the applicator being adapted for delivery of laser radiation from the fiber laser to an area of interest the applicator comprising an endoscopic fiber or bare fiber;
wherein the fiber laser comprises a doped fiber as active medium for generation of laser radiation having a wavelength in the range of 1.6 µm to 2.4 µm;
wherein the doped fiber is a Thulium doped fiber, and
wherein the doped fiber has a diameter in the range of 5 µm to 600 µm; and
wherein the endoscopic or bare fiber and the doped fiber are formed by a single fiber.

18. System according to claim 17, wherein the laser radiation has a wavelength in the range of 1.92 µm to 1.96 µm.

19. The system of claim 17, wherein the doped fiber is coiled within a housing and activated by a plurality of laser diodes.

20. The system of claim 19, further comprising a controller positioned within the housing, the controller controlling a power supply that supplies power to the plurality of laser diodes to control characteristics of the laser radiation generated by the doped fiber.

21. A system, comprising:
a fiber laser for generation of laser radiation, the fiber laser comprising:
an active fiber coiled within a housing, and
at least one laser diode positioned within the housing, the at least one laser diode being in communication with the active fiber in order to pump the active fiber with radiation; and
an applicator coupled with the fiber laser, the applicator being adapted for delivery of laser radiation from the fiber laser to an area of interest, wherein the applicator comprises an endoscopic fiber or bare fiber.

22. The system of claim 21, wherein the endoscopic or bare fiber is coupled with the fiber laser and the applicator for transmission of the laser radiation from the fiber laser to the applicator.

23. The system of claim 21, wherein the active fiber comprises a doped fiber as an active medium for generation of laser radiation having a wavelength in the range of 1.6 µm to 2.4 µm.

24. The system of claim 23, wherein
the active fiber is a Thulium doped fiber, and
the active fiber has a diameter in the range of 5 µm to 600 µm.

25. The system of claim 23 wherein the active fiber comprises a first connector and the endoscopic or bare fiber comprises a second connector, the second connector for coupling with the first connector of the active fiber.

26. The system of claim 23, wherein the endoscopic or bare fiber and the active fiber are formed by a single fiber.

27. The system of claim 23, wherein the laser radiation has a wavelength in the range of 1.92 μm to 1.96 μm.

28. The system of claim 21, further comprising at least one of the following:

wherein the fiber laser is adapted for generation of laser radiation having a laser energy in the range of 5 W to 30 W, wherein the fiber laser is adapted for generation of pulsed laser radiation having a pulse duration in the range of 0.5 ms to 20 ms, wherein the fiber laser has a duty cycle in the range of 10% to 100%, and wherein the fiber laser is adapted for generation of continuous laser radiation.

* * * * *